(12) United States Patent
Spireas

(10) Patent No.: US 7,056,951 B2
(45) Date of Patent: Jun. 6, 2006

(54) STABLE SOLID DOSAGE FORMS OF AMINO ACIDS AND PROCESSES FOR PRODUCING SAME

(75) Inventor: Spiridon Spireas, Newtown, PA (US)

(73) Assignee: Mutual Pharmaceutical Co., Inc., Philadelphia, PA (US)

( * ) Notice: Subject to any disclaimer, the term of this patent is extended or adjusted under 35 U.S.C. 154(b) by 0 days.

(21) Appl. No.: 09/928,467

(22) Filed: Aug. 13, 2001

(65) Prior Publication Data

US 2002/0091159 A1 Jul. 11, 2002

Related U.S. Application Data

(60) Provisional application No. 60/235,349, filed on Sep. 26, 2000.

(51) Int. Cl.
*A61K 31/196* (2006.01)
*A61K 47/04* (2006.01)
*A61K 47/10* (2006.01)
*A61K 47/08* (2006.01)

(52) U.S. Cl. .................... 514/561; 424/400; 514/970

(58) Field of Classification Search ............... 514/561, 514/974, 970; 424/464, 488, 489, 400; 562/433, 562/443

See application file for complete search history.

(56) References Cited

U.S. PATENT DOCUMENTS

| 4,035,507 | A | 7/1977 | Bodor et al. ............ 424/311 |
| 4,087,544 | A | 5/1978 | Satzinger et al. ........ 424/305 |
| 5,084,479 | A | 1/1992 | Woodruff ............... 514/530 |
| 5,800,834 | A | 9/1998 | Spireas et al. ........... 524/451 |
| 5,906,832 | A | 5/1999 | Jao et al. ............... 424/465 |
| 6,054,482 | A | 4/2000 | Augart et al. ........... 514/561 |
| 6,294,198 | B1 | 9/2001 | Vilkov ................. 424/465 |
| 6,531,509 | B1 | 3/2003 | Singer et al. ........... 514/561 |
| 2002/0061931 | A1 | 5/2002 | Singer et al. ........... 514/561 |

FOREIGN PATENT DOCUMENTS

| CA | 2 410 867 | 12/2001 |
| EP | 0 414 263 A2 | 2/1991 |
| WO | WO 98/28255 | 7/1998 |
| WO | WO 99/59572 | 11/1999 |
| WO | WO 99/59573 | 11/1999 |
| WO | WO 00/07568 | 2/2000 |
| WO | WO 01/13894 A1 | 3/2001 |
| WO | WO 01/97612 A1 | 12/2001 |
| WO | WO 01/97782 A1 | 12/2001 |

OTHER PUBLICATIONS

Theory & Practice of Industrial Pharmacy, 3rd Edition, Liberman, Lachman, and Kanig, eds., (Philadelphia, Pennsylvania: Lea & Febiger).

*Primary Examiner*—Edward J. Webman
(74) *Attorney, Agent, or Firm*—Woodcock Washburn, LLP

(57) ABSTRACT

Pharmaceutical formulations, and processes for making same, comprising an amino acid which is liable to formation of an undesirable lactam, and a stabilizer comprising a volatile alcohol; a non-volatile alcohol; a water immiscible liquid or solid; a liquid with a relatively low dielectric constant; a liquid surface active agent; a solid surface active agent; an antioxidant; a ketone; an aldehyde; a solid polyethylene glycol of high molecular weight; polyvinylpyrrolidone; a derived cellulose; silicon dioxide; or a combination thereof.

20 Claims, No Drawings

STABLE SOLID DOSAGE FORMS OF AMINO ACIDS AND PROCESSES FOR PRODUCING SAME

CROSS REFERENCE TO RELATED APPLICATIONS

This application claims benefit of U.S. provisional application, Ser. No. 60/235,349 filed Sep. 26, 2000, the contents of which is hereby incorporated herein by reference in its entirety.

FIELD OF THE INVENTION

The present invention relates to pharmaceutical formulations and processes for producing the same. In particular, the present invention relates to stable pharmaceutical solid dosage formulations comprising amino acids and processes for producing the same.

BACKGROUND OF THE INVENTION

Cyclic amino acids of general Formula I:

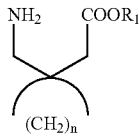

wherein $R_1$ is H or a lower alkyl radical and n is 4, 5, or 6, are known to be useful in the treatment of certain cerebral and neurodegenerative diseases. See, e.g., U.S. Pat. Nos. 4,087,544 and 5,084,479, which are incorporated herein by reference in their entireties. For example, when $R_1$ is hydrogen and n is 5, the cyclic amino acid is 1-(aminomethyl)-1-cyclohexaneacetic acid, which is also known as gabapentin. Gabpentin has been shown to be useful as an anticonvulsant agent.

However, the use of such cyclic amino acids in the preparation of medicaments has been limited because such cyclic amino acids easily degrade during storage. The degradable is believed to be due, at least in part, to conversion of the cyclic amino acid to its lactam of Formula II:

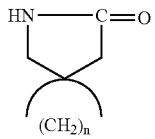

The lactams of Formula II are particularly undesirable in the preparation of medicaments because of their relatively high toxicities, as compared to the cyclic amino acids of Formula I. To reduce the concentration of lactam, the cyclic amino acids of Formula I are typically treated with a mineral acid, for example hydrochloric acid. For example, when gabapentin is treated with a semi-concentrated solution of hydrochloric acid (HCl), the lactam is hydrolyzed and converted back to the pure gabapentin form. In other words, the treatment with HCl constitutes a purification process of gabapentin necessary to eliminate the lactam impurity.

However, the purification of cyclic amino acids of Formula I with a mineral acid leaves residual mineral acid anions in contact with the purified cyclic amino acid. Although the mineral acid is needed to convert the lactam to its cyclic amino acid form, the continued presence of the mineral acid anions causes the purified cyclic amino acid to form its corresponding lactam upon storage. Without being bound by theory, it is believed that the highly ionizable, electronegative mineral acid anion, being in close proximity to the cyclic amino acid and surrounded by the surfaces of compressed powder excipients (which are typically used in the preparation of medicaments), displays the tendency to attract water in the form of hydronium ions ($H_3O^+$) in order to remain coupled in its thermodynamically stable state, e.g., ($H_3O^+$)($Cl^-$). Re-cyclization of the cyclic amino acid to form the lactam impurity provides the water molecules necessary for creation of the thermodynamically stable state described above.

In the past, the rate at which the purified cyclic amino acid degrades to form the lactam impurity was decelerated by carefully controlling the amount of residual mineral acid anions present. For example, U.S. Pat. No. 6,054,482 (the 482 patent), which is incorporated herein by reference in its entirety, describes a pharmaceutical composition containing: i) an active ingredient such as gabapentin in the free amino acid, crystalline anhydrous form containing less than 0.5% by weight of its corresponding lactam and less than 20 ppm of an anion of a mineral acid, and ii) one or more pharmaceutically acceptable adjuvants that do not promote conversion of more than 0.2% by weight of the gabapentin to its corresponding lactam form when stored at 25° C. and an atmospheric humidity of 50% for one year. However, controlling the amount of residual mineral acid anion is both expensive and time consuming. The '482 patent also discloses the use of certain, inert powder excipients to further stabilize the amino acid with respect to its lactam. However, it is known that the use of the disclosed excipients in formulations having 20 ppm or more of the mineral acid anion do not provide acceptably stable solid dosage forms of the amino acid. Hence, compositions and methods which address these needs have long been sought.

SUMMARY OF THE INVENTION

The present invention relates to pharmaceutical formulations, solid dosage forms comprising the pharmaceutical formulations, and processes for producing the same. The formulations contain amino acids which are substantially free of their corresponding lactams. The formulations are sufficiently stable upon storage, even, for example, in the presence of electronegative ions greater than 20 ppm. Further, the compositions and processes provide pharmaceutical formulations wherein the amino acids are stabilized even in the presence of anions from a mineral acid.

In one of its aspects, the present invention relates to pharmaceutical formulations comprising one or more amino acids, which are susceptible to formation of undesirable lactams, and a stabilizer to inhibit the formation of such lactams. The stabilizer comprises a volatile alcohol, a non-volatile alcohol, a non-volatile liquid, water miscible liquid or solid, a water immiscible liquid or solid, a liquid with a low dielectric constant, a liquid surface active agent; a solid surface active agent, an antioxidant, a ketone, an aldehyde, a solid polyethylene glycol of high molecular weight, polyvinylpyrrolidone, an silicon dioxide, or combinations thereof.

Amino acids useful with the present invention include cyclic amino acids of the formula:

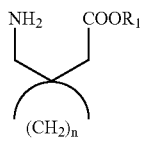

wherein $R_1$ is selected from the group consisting of hydrogen and a lower alkyl and n is an integer from about 4 to about 6. In one particular embodiment, the amino acid is in a crystalline anhydrous form.

The formulation optionally further includes one or more adjuvants for enhancing the handling of the pharmaceutical formulation. Preferably, the adjuvant is a pharmaceutically acceptable adjuvant that reduces the degredation of amino acids. The adjuvants of the present invention include, but are not limited to, a pharmaceutically acceptable excipient, such as a modified cellulose, a microcrystalline cellulose, a starch, a sodium starch glycolate, talc, stearates, or a combination thereof.

The formulations of the present invention can be processed into a stable solid dosage form. Suitable solid dosage forms include, but are not limited to, tablets, coated tablets, caplets, beads, capsules, hard shell gelatin capsules, or hard shell HPMC capsules.

In another of its aspects, the present invention relates to pharmaceutical formulations comprising one or more amino acids, which are susceptible to formation of undesirable lactams; electronegative ions; and one or more stabilizers to inhibit the formation of such lactams.

In preferred embodiments, the electronegative ions are anions from mineral acids. Preferably, the anion is Cl⁻ obtained from hydrochloric acid, present in an amount of more than about 20 ppm. The lactam is preferably present in an amount less than about 0.8%, more preferably less than about 0.4%, even more preferably less than about 0.25%, and still more preferably less than about 0.15% by weight of the active ingredient. The formulation also optionally includes one or more adjuvants.

In yet another embodiment, the present invention relates to a process for forming pharmaceutical formulations wherein one or more amino acids, which are susceptible to formation of undesirable lactams with mineral acids, are treated with one or more stabilizers to inhibit the formation of such lactams. The amino acids are optionally treated with one or more mineral acids and optionally washed to remove at least a portion of the mineral acids. The amino acids can be treated with the stabilizers during purification of the amino acids to form purified amino acids, during granulation of the amino acids, or both.

DETAILED DESCRIPTION OF PREFERRED EMBODIMENTS

The present invention relates to pharmaceutical formulations comprising at least one amino acid that is capable of forming an undesirable lactam impurity and one or more stabilizers for stabilizing the amino acid and avoiding formation of the lactam impurity. The compositions also optionally include one or more adjuvants for enhancing the handling and/or manufacturing of the amino acid into an acceptably uniform, flowable, and compressible admixture.

The pharmaceutical formulations of the present invention include amino acids which are substantially free of their corresponding lactam impurities. Further, the amino acids comprising the formulations of the present invention are stabilized even in the presence of electronegative ions. For example, stable solid dosage forms of the amino acid formulations are stable even in electronegative ion concentrations greater than 20 ppm. In particular, the present invention provides sufficiently stable solid dosage forms of an amino acid known to undergo cyclization. As a non-limiting example, the present invention provides stable dosage forms of 1-aminomethyl-1-cyclohexaneacetic acid (gabapentin) in its free amino acid, anhydrous crystalline form, or polymorphic forms, even in the presence of more than 20 ppm of anions such as chloride ions (Cl⁻) coming from a mineral acid such as hydrochloric acid (HCl). The formulations are also sufficiently stable upon storage.

The term "sufficiently stable" refers to solid dosage forms which, when stored for 90 days (3 months) in plastic HDPE (High Density PolyEthylene plastic) bottles without desiccant at 40° C. and 75% relative humidity (RH), degrade due to hydrolysis, reduction or cyclization of their contained amino acid to its corresponding lactam impurity yielding preferably not more than about 2.0%, more preferably not more than about 0.8%, more preferably not more than about 0.6%, even more preferably not more than about 0.4%, still more preferably not more than about 0.25% and yet more preferably not more than about 0.15% of lactam impurity.

Alternatively, "sufficiently stable" dosage forms are dosage forms which, when stored for 10 days in plastic HDPE bottles without desiccant at 60° C. and 75% relative humidity (and provided that no adverse effect was observed on the dosage form due to heating), yield preferably not more than about 1%, more preferably not more than about 0.8%, even more preferably not more than about 0.6%, still more preferably not more than about 0.45% and yet more preferably not more than about 0.3% of lactam impurity.

In yet another embodiment, "sufficiently stable" dosage forms are dosage forms which, when stored for 20 days in plastic HDPE bottles without desiccant at 60° C. and 75% relative humidity (and provided that no adverse effect was observed on the dosage form due to heating), yield preferably not more than about 2.5%, more preferably not more than about 2%, even more preferably not more than about 1.5%, still more preferably not more than about 1% and yet more preferably not more than about 0.6% of lactam impurity.

The term "lactam impurity" refers to an unwanted degradation product of an amino acid. For example, gabapentin is known to undergo unwanted cyclization due to dehydration of its molecules. The cyclization product of the amino acid is its corresponding lactam impurity.

Amino acids useful with the present invention include amino acids which may degrade in their solid states by a dehydration process leading to cyclization to form a lactam. In particular, suitable amino acids include cyclic amino acids of Formula I:

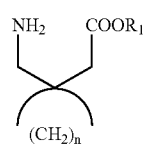

I wherein $R_1$ is a lower alkyl and n is an integer between about 4 and about 6. For example, $R_1$ is a straight or branched chain alkyl group having up to about 8 carbon atoms.

Preferred compounds of Formula I include, but are not limited to, 1-aminomethyl-1-cycloheaxaneacetic acid, ethyl 1-aminomethyl-1-cyclohexane acetate, 1-aminomethyl-1-cycloheptaneacetic acid, 1-aminomethyl-1-cyclopentaneaceteic acid, methyl 1-aminomethyl-1-cyclohexane acetate, n-butyl 1-aminomethyl-1-cyclohexane acetate, methyl 1-aminomethyl-1-cycloheptane acetate, n-butyl 1-aminomethyl-1-cycloheptane acetate, toluene sulfonate, 1-aminomethyl-1-cyclopentane acetate, benzene sulfonate, and n-butyl 1-aminomethyl-1-cyclopentane acetate. A particularly preferred compound of Formula I is 1-aminomethyl-1-cyclohexaneacetic acid (gabapentin).

The amino acids useful with the present invention also include compounds of the formula:

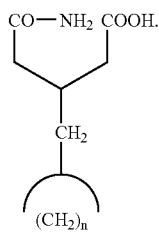

For example, suitable amino acids for use in the present invention include those compounds disclosed in U.S. Pat. No. 4,035,507, which is incorporated herein by reference in its entirety.

The stabilizers used in accordance with the present invention include pharmaceutically acceptable compounds which reduce or inhibit hydrolysis, reduction or the formation of the lactam forms of the amino acids used in the pharmaceutical formulations. In particular, suitable stabilizers include compounds which will reduce or inhibit ionic activity due to the high electronegativity and the tendency of contained anions (e.g., anions produced from mineral acids) to attract water.

For example, suitable stabilizers include, but are not limited to, semipolar or nonpolar, volatile or non-volatile compounds such as alcohols (e.g., methanol, ethanol, propanol, and isopropanol (IPA)); non-volatile liquids (e.g., propylene glycol, glycerine, Polysorbate 80, and Polyethylene Glycol 400); water miscible liquids and solids, water immisible liquids and solids such as oils (e.g., olive oil) and fatty acids (e.g., stearic acid); liquids with low dielectric constants; liquid surface active agents; solid surface active agents; antioxidants such as butylated hydorxy-anisole (BHA), ascorbic acid, and stearic acid; ketones (e.g., acetone); aldehydes; Povidone® (available from International Specialty Products, Wayne, N.J.); solid polyethylene glycols of high molecular wight; polyvinylpyrrolidone; various types of derived cellulose (e.g., hydroxypropylmethyl cellulose, hydroxypropyl cellulose, ethyl cellulose, sodium carboxymethyl cellulose, and others); silicon dioxide; or combinations thereof.

For example, minute quantities of Butylated Hydroxyanisole, NF or Povidone®, USP, dissolved in ethyl alcohol, can be utilized. However, polar solvents possessing high dielectric constants and enhancing the electronegativity and ionic activity of the $Cl^-$ ions, such as water, are preferably avoided. However, other compounds that inhibit or diminish ionic activity resulting in dehydration and cyclization of the amino acid to its corresponding lactam impurity could also be used as a stabilizer in the present invention.

Dielectric constants measure the ability of a substance to store electrical potential energy under the influence of an electric field. The magnitude of dielectric constants has a significant effect on the strength of interactions between ions in solution. Dielectric constants increase as the molecules of a substance are polar and easily polarizable. In some embodiments, the stabilizer having a low dielectric constant comprises a liquid with a dielectric constant below 60, more preferably the dielectric constant is below about 45, even more preferably the dielectric constant is below 30.

The term "trace amounts" of volatile stabilizer refers to minute quantities of any stabilizer remaining in the pharmaceutical composition even if the stabilizer used to treat the amino acid and/or the formulation is a volatile liquid with a boiling point less than 100° C. It should be emphasized that, even when a volatile liquid stabilizer is used, some residual trace amounts of the stabilizer will remain in the dosage form surrounding the amino acid and diminishing the tendency for water attraction displayed by the anions ($Cl^-$) of a mineral acid (HCl) attached to the crystals of the amino acid. Preferably, trace amounts of stabilizer range from about 0% to about 2.5%, more preferably from about 0% to about 1.0%, and even more preferably from about 0% to about 0.5% by weight of the final powder blend. Even if the amino acid is treated with volatile stabilizers, the main bulk of which will be finally evaporated at the end of the manufacturing process, it is expected that trace amounts of the stabilizers will remain in the composition exerting their stability-enhancement properties.

The adjuvants used in accordance with the present invention include pharmaceutically acceptable compounds which are intended to enhance the handling and/or manufacturing of the pharmaceutical formulations into an acceptably uniform, flowable and compressible admixture which can be readily produced into the final dosage form. By "pharmaceutically acceptable" is meant a material which is not biologically or otherwise undesirable, i.e., the material can be administered to an individual along with the active ingredient formulation without causing any undesirable biological effects or interacting in a deleterious manner with any of the components of the formulation in which it is contained.

For example, adjuvants include pharmaceutically acceptable excipients, such as powder excipients. The term "excipient" includes, but is not limited to, the family of modified celluloses such as carboxymethyl and ethyl cellulose, hydroxyethyl cellulose, microcrystalline cellulose and others. The FMC Company offers a line of such excipients under its Avicel® brand name. In one embodiment, the excipient is at least one of microcrystalline cellulose, starch (e.g., corn starch), talc, and sodium starch glycolate.

Those of skill in the art will also understand that the term "excipient" is used colloquially to include such agents as disintegrating agents, carriers, diluents, pigments, binders, colorants, lubricants, and adsorbent/coating materials. In one embodiment, the excipient is a disintegrating agent. The term "disintegrating agent" is well known to those of skill in the art as an agent that enhances the conversion of a compact material into fine primary particles during dissolution. Disintegrating agents include, but are not limited to, starch, cellulose, sodium starch glycolate, modified cellulose, and crosslinked POVIDONE® (available from International Specialty Products, Wayne, N.J.).

The term "lubricant" is well known to those of skill in the art as an additive to prevent the sticking of the formulation to tooling during the tableting process. Lubricants include, but are not limited to, stearates (especially magnesium stearate), hydrogenated vegetable oils, and talc. In preferred embodiments, the lubricant is talc.

The term "binder" is well known to those of skill in the art as an agent that holds the components of the formulation together. Binders include, but are not limited to, gelatin, polyvinylpyrrolidone (PVP), hydroxypropylmethylcellulose (HPMC), starch grades (pregelatinized or plain), hydroxypropylcellulose (HPC), and carboxymethylcellulose (CMC).

In addition, when the stabilized formulations contain nonvolatile liquids such as propylene glycol, polysorbate 80, polyethylene glycol 400 and olive oil, minute quantities of silica (Syloid 244 FP) as an adsorbent/coating material according to the principles of Liquisolid Systems described in several U.S. and international patents such as U.S. Pat. No. 5,800,834, can be used in compositions which have been first treated with the aforementioned nonvolatile liquid stabilizers.

As used herein, the term "pharmaceutical solid dosage forms" refers to the final solid pharmaceutical product. The pharmaceutical formulations of the present invention can be formed into any of a variety of dosage forms including, but not limited to, tablets, coated tablets, caplets, beads, capsules, or hard shell gelatin capsules, or hard shell HPMC capsules.

The present invention further relates to processes for producing pharmaceutical compositions from amino acids which are susceptible to hydrolysis, reduction, or formation of an undesirable lactam. The processes include the step of treating or mixing an amino acid which is susceptible to formation of an undesirable lactam impurity with a mineral acid, such as hydrochloric acid. In one particular embodiment, the amino acid is a cyclic amino acid of Formula I. Such cyclic amino acids can be prepared using any of a variety of conventional techniques. For example, gabapentin can be formulated by converting a compound of the formula:

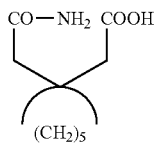

via a reactive acid derivative thereof, into an azide which is then subjected to a Curtius rearrangement; or by subjecting the compound of the above formula to a Hoffmann rearrangement; or by subjecting a compound of the formula:

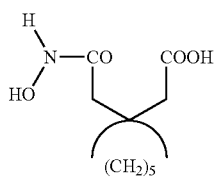

to a Lossen rearrangement, as described in U.S. Pat. No. 4,087,544, which is incorporated herein by reference in its entirety.

The treated amino acid is then optionally dried and compounded or granulated with a stabilizer to inhibit the formation of such lactam. The granulating step is optionally performed in the presence of one or more adjuvants which are added to enhance certain properties of the resulting pharmaceutical formulation. In some instances, the drug is pretreated with the stabilizers first, and then it is mixed with the adjuvants to produce the final powder blend. In other cases, the treated drug and at least one adjuvant such as corn starch, are blended and then treated again by other stabilizers yielding a product, which is then blended with another adjuvant such as talc to produce the final powder blend. In some preferred embodiments the adjuvants are inert and do not accelerate cylization of amino acids. In some embodiments, the main stabilization action is due to the stabilizers of the present invention and not due to the adjuvants used.

The granulated product can then be formed into any of a variety of dosage forms. The processes of mixing, drying, granulating and making pharmaceutical formulations are well known to those of skill in the art. See, e.g., Theory & Practice of Industrial Pharmacy, $3^{rd}$ Edition, Liberman, Lachman, and Kanig, eds. (Philadelphia, Pa.: Lea & Febiger), incorporated herein by reference.

Examples

Tests were conducted to determine the ability of the present invention to provide stable pharmaceutical formulations. Tests were conducted with formulations containing an amino acid that is susceptible to formation of an undesirable lactam impurity in the presence of electronegative ions. Although the tests use pharmaceutical formulations comprising gabapentin in the presence of $Cl^-$ anions, the stabilization of other active agents is contemplated by the present invention.

Several anhydrous gabapentin capsule formulations (Example 1–35) containing different forms of the drug with less or more than 20 ppm of $Cl^-$ anions attached in its crystals, were prepared in batches of 2,500 units. Each unit (hard-shell gelatin capsule) was targeted to contain 400 mg of the drug. All mixing and wet granulation procedures were conducted in a 10 L Collette Gral High Shear Mixer/Granulator, and all final powders were encapsulated in a semi-manual MiniCap Encapsulator. In all, 35 examples (Exs. 1–35) were made. The formulations corresponding to Exs. 1–35 are shown in Tables 1–5. In addition, a commercial source of gabapentin (Neurontin available from Pfizer, Inc.) was obtained and used as a comparative example (Comp. Ex. A). Neurontin contains mostly monohydrate crystals of gabapentin.

TABLE 1

| Ingredients (mg per unit dose) | Comp. Ex. A** | Ex. 1 | Ex. 2 | Ex. 3 |
|---|---|---|---|---|
| Gabapentin Monohydrate | 400 | — | — | — |
| Gabapentin Anhydrous (less than 20 ppm HCl) | — | 400 | — | — |
| *Purified-alc-HCl Gabapentin (using Alcoholic HCl) | — | — | 400 | — |
| *Purified-aq-HCl Gabapentin (using Aqueous HCl) | — | — | — | 400 |
| Corn starch, NF (purity 826) | — | 113 | 113 | 113 |
| Talc, USP | — | 27 | 27 | 27 |

*Contains more than 50 ppm HCl and trace amounts of the volatile liquid vehicle used to prepare the HCl solution, alcohol or water in this example.

TABLE 1-continued

| Ingredients (mg per unit dose) | Comp. Ex. A** | Ex. 1 | Ex. 2 | Ex. 3 |
|---|---|---|---|---|

**Commercial product (Neurontin, Lot #10189V) known to contain gabapentin monohydrate; no information other than that given by the Physician's Desk Reference was available regarding the commercial product's preparation and inactive ingredients.

TABLE 2

| Ingredients (mg per unit dose) | Ex. 4 | Ex. 5 | Ex. 6 | Ex. 7 | Ex. 8 | Ex. 9 | Ex. 10 | Ex. 11 |
|---|---|---|---|---|---|---|---|---|
| *Anhydrous Gabapentin | 400 | — | — | 400 | — | — | — | — |
| **Purified-alc-HCl Gabapentin | — | 400 | — | — | 400 | — | 400 | — |

TABLE 2-continued

| Ingredients (mg per unit dose) | Ex. 4 | Ex. 5 | Ex. 6 | Ex. 7 | Ex. 8 | Ex. 9 | Ex. 10 | Ex. 11 |
|---|---|---|---|---|---|---|---|---|
| **Purified-aq-HCl Gabapentin | — | — | 400 | — | 400 | — | 400 | |
| Cornstarch, NF (purity 826) | 113 | 113 | 113 | 113 | 113 | 113 | 113 | 113 |
| Talc, USP | 27 | 27 | 27 | 27 | 27 | 27 | 27 | 27 |
| Denatured Alcohol*** | 100 | 100 | 100 | — | — | — | — | — |
| Purified Water*** | — | — | — | 100 | 100 | 100 | — | — |
| Acetone*** | — | — | — | — | — | — | 100 | 100 |

*Contains less than 20 ppm HCl.
**Contains more than 50 ppm HCl.
***Present in trace amounts in the final product.

TABLE 3

| Ingredients (mg per unit dose) | Ex. 12 | Ex. 13 | Ex. 14 | Ex. 15 | Ex. 16 | Ex. 17 | Ex. 18 |
|---|---|---|---|---|---|---|---|
| Purified-alc-HCl Gabapentin | 400 | 400 | 400 | 400 | 400 | 400 | 400 |
| Cornstarch, NF (purity 826) | 103 | 100 | 103 | 103 | 100 | 103 | 100 |
| Talc, USP | 27 | 27 | 27 | 27 | 27 | 27 | 27 |
| Denatured Alcohol* | 88 | 100 | 88 | 88 | 100 | 88 | 100 |
| Butylated Hydroxyanisole, NF | 10 | 10 | — | — | — | — | — |
| Polysorbate 80, NF | — | — | 10 | — | — | — | — |
| Polyethylene Glycol 400, NF | — | — | — | 10 | 10 | — | — |
| Propylene Glycol, NF | — | — | — | — | — | 10 | — |
| EDTA | — | — | — | — | — | — | 10 |
| Ascorbic Acid | — | — | — | — | — | — | 3 |
| Silica (Syloid 244 FP) | — | — | — | — | 3 | — | — |
| Povidone (PVP K29/32) | — | 3 | — | — | — | — | — |

*Present in trace amounts in the final product.

TABLE 4

| Ingredients (mg per unit dose) | Ex. 19 | Ex. 20 | Ex. 21 | Ex. 22 | Ex. 23 | Ex. 24 | Ex. 25 |
|---|---|---|---|---|---|---|---|
| Purified-aq-HCl Gabapentin | 400 | 400 | 400 | 400 | 400 | 400 | 400 |
| Cornstarch, NF (purity 826) | 103 | 100 | 103 | 103 | 100 | 103 | 100 |
| Talc, USP | 27 | 27 | 27 | 27 | 27 | 27 | 27 |
| Denatured Alcohol* | 100 | 100 | 100 | 100 | 100 | 100 | 100 |
| Butylated Hydroxyanisole, NF | 10 | 10 | — | — | — | — | — |
| Polysorbate 80, NF | — | — | 10 | — | — | — | — |
| Polyethylene Glycol 400, NF | — | — | — | 10 | 10 | — | — |
| Propylene Glycol, NF | — | — | — | — | — | 25 | — |
| EDTA | — | — | — | — | — | — | 10 |
| Ascorbic Acid | — | — | — | — | — | — | 3 |
| Silica (Syloid 244 FP) | — | — | — | — | 3 | — | — |
| Povidone (PVP K29/32) | — | 3 | — | — | — | — | — |

*Present in trace amounts in the final product.

TABLE 5

| Ingredients (mg per unit dose) | Ex. 26 | Ex. 27 | Ex. 28 | Ex. 29 | Ex. 30 | Ex. 31 | Ex. 32 | Ex. 33 | Ex. 34 | Ex. 35 |
|---|---|---|---|---|---|---|---|---|---|---|
| Purified-alc-HCl Gabapentin | 400 | — | 400 | — | 400 | — | 400 | — | 400 | — |
| Purified-aq-HCl Gabapentin | — | 400 | — | 400 | — | 400 | — | 400 | — | 400 |
| Cornstarch, NF | 103 | 103 | 103 | 103 | 100 | 100 | 100 | 100 | 103 | 103 |

TABLE 5-continued

| Ingredients (mg per unit dose) | Ex. 26 | Ex. 27 | Ex. 28 | Ex. 29 | Ex. 30 | Ex. 31 | Ex. 32 | Ex. 33 | Ex. 34 | Ex. 35 |
|---|---|---|---|---|---|---|---|---|---|---|
| (purity 826) | | | | | | | | | | |
| Talc, USP | 27 | 27 | 27 | 27 | 27 | 27 | 27 | 27 | 27 | 27 |
| Acetone* | 100 | 100 | 100 | 100 | 100 | 100 | — | — | — | — |
| Purified Water* | — | — | — | — | — | — | 100 | 100 | 100 | 100 |
| Olive Oil, NF | 10 | 10 | — | — | — | — | — | — | — | — |
| Polyethylene Glycol 400, NF | — | — | — | — | 10 | 10 | — | — | — | — |
| Propylene Glycol, NF | — | — | 10 | 10 | — | — | — | — | 10 | 10 |
| EDTA | — | — | — | — | — | — | 10 | 10 | — | — |
| Ascorbic Acid | — | — | — | — | — | — | 3 | 3 | — | — |
| Silica (Syloid 244 FP) | — | — | — | — | 3 | 3 | — | — | — | — |

*Present in trace amounts in the final product.

The original anhydrous gabapentin raw material was manufactured by Teva-Tech, Limited and distributed by Plantex USA, Inc., with a manufacturer's lot number of 288071799. Titration analysis of the original anhydrous gabapentin material revealed that it contained approximately 15 ppm of Cl$^-$ anions. Subsequently, portions of this raw material were treated with an alcoholic or aqueous 0.005M HCl solution to produce two types of Purified Gabapentin containing about 55 ppm of Cl$^-$ anions. Specifically, two 17.5-kg portions of the original gabapentin raw material were granulated separately in a 75 L Collette Gral High Shear Mixer/Granulator with either an alcohol 0.005M HCl solution or an aqueous 0.005M HCl solution, to yield after drying, what is referred to in Tables 1–5 as "Purified Gabapentin." Depending on the type of HCl solution used, i.e., alcoholic or aqueous, the produced drug is abbreviated herein as "purified-alc-HCl gabapentin" and "purified-aq-HCl gabapentin," respectively. Both terms "ppm Cl$^-$" and "ppm HCl" refer to the concentration, in parts per million (ppm), of chloride ions (Cl$^-$ anions) attached to the amino acid crystals such as those of anhydrous gabapentin. Such Cl$^-$ anions originate from the mineral acid (e.g., HCl) and remain as residual amounts on the crystals of the drug. Without being bound by any particular theory, it is believed that residual Cl$^-$ anions and their ionic attraction of water molecules are one of the main reasons for the dehydration of the amino acid molecules resulting in their cyclization to the unwanted lactam impurity.

As applicable to a unit-dose basis, 80 mg of the alcoholic HCl solution was mixed with 400 mg of drug expected to leave, after drying, a residual HCl amount attached on the drug crystals reaching a net concentration of 40 ppm of Cl$^-$ ions. Such concentration of Cl$^-$ added to the already existing levels of the original gabapentin raw material (about 15 ppm) brought the total residual HCl concentration to about 55 ppm of Cl$^-$ ions contained by the final anhydrous gabapentin treated with the alcoholic HCl solution. On the other hand, 100 mg of the aqueous HCl solution were mixed with 400 mg of drug (unit dose) expected to also leave, after drying, a residual HCl amount attached on the drug crystals reaching a net concentration of 40 ppm of Cl$^-$ ions. Again, such concentration of Cl$^-$ ions added to the already existing levels of the original gabapentin raw material (15 ppm) brought the total residual HCl concentration to about 55 ppm of Cl$^-$ ions contained in the final anhydrous gabapentin treated with the aqueous HCl solution.

The two purified anhydrous gabapentin materials containing more than 50 ppm of HCl and the original anhydrous gabapentin raw material containing less than 20 ppm of HCl, were used to prepare several capsule formulations using different compositions and manufacturing techniques including dry-mixing, and granulations of either alcohol, water and acetone alone or solutions/dispersions of various additives in alcohol, water and acetone. Whenever granulations were made, a standard 100-mg per unit dose of the volatile granulating liquid (alcohol, water or acetone) was used. Furthermore, in certain formulations, two excipients (corn starch, NF (purity 826) and talc, USP) were used. The quantities of these two pharmaceutically acceptable adjuvants were almost always constant in the capsule formulations, namely, about 113 mg of corn starch per unit dose and about 27 mg of Talc per unit dose.

Examples 1–3 listed in Table 1 are dry blends containing similar inactive powder adjuvants and three different types of gabapentin. Example 1 contains the originally received anhydrous gabapentin with less than 20 ppm of HCl (about 15 ppm Cl$^-$), whereas example 2 and 3 contain the purified-alc-HCl gabapentin and the purified-aq-HCl gabapentin, respectively, both with about 55 ppm of Cl$^-$ ions attached to the gabapentin crystals. All three examples contain standard amounts of two powder adjuvants as shown in Table 1, which were mixed with the drug in the following sequence. The drug and corn starch were first passed through a 20-mesh stainless steel screen and then dry-mixed in a plastic bag for 5 minutes. The talc was then added in the same bag after being passed through a 20-mesh stainless steel screen and mixed with the drug/starch blend for another 3 minutes to produce the final powder blend which was encapsulated in No. 0-size hard-shell gelatin capsules with a fill weight of 540 mg of powder per capsule.

Examples 4–11 listed in Table 2 are wet granulations containing similar inactive powder adjuvants, three different types of gabapentin and three different volatile granulating liquids, namely, ethyl alcohol, water and acetone. Specifically, examples 4 and 7 contain the originally received anhydrous gabapentin with less than 20 ppm of HCl (about 15 ppm Cl$^-$), examples 5, 8 and 10 contain the purified-alc-HCl gabapentin with about 55 ppm of HCl, and examples 6, 9 and 11 contain the purified-aq-HCl gabapentin also with about 55 ppm of Cl$^-$ ions attached to the drug crystals. Examples 4–11 contain standard amounts of two powder adjuvants as shown in Table 2, which were mixed with the drug in the following sequence. The drug and corn starch were first mixed for 5 minutes in a 10 L Collette Gral High Shear Mixer/Granulator and then, the corresponding granulating liquid was added to granulate the powder blend over a period of 4 minutes. After drying, the granulation was passed through a 20mesh stainless steel screen and placed in a plastic bag. The talc was then added in the same bag after being passed through a 20-mesh stainless steel screen and mixed with the drug/starch dried granulation for 3 minutes to produce the final powder blend which was encapsulated in No. 0-size hard-shell gelatin capsules with a fill weight of 540 mg of powder per capsule.

Examples 12–18 listed in Table 3 are alcoholic granulations containing similar inactive powder adjuvants and the same type of anhydrous gabapentin containing about 55 ppm of Cl⁻ ions after being treated with an alcoholic 0.005M HCl solution, i.e., purified-alc-HCl gabapentin. All capsule formulations of Table 3 were made in a manner almost identical to that of example 5 of Table 2. However, with examples 12–18, various nonvolatile liquid or solid additives expected to perform as possible stabilizers were incorporated in the volatile granulating liquid, i.e., ethyl alcohol, to make a solution or dispersion which was then used to granulate the drug/starch blend of each capsule formulation of examples 12–18.

Examples 19–25 listed in Table 4 are alcoholic granulations similar to those of Table 3. However, these capsule formulations (Exs. 19–25) contain gabapentin with about 55 ppm of Cl⁻ ions after being treated with an aqueous 0.005M HCl solution, i.e., purified-aq-HCl gabapentin. As with the examples of Table 3, the capsule formulations of examples 19–25 contain similar inactive powder adjuvants and the same type of drug. The capsule formulations of Table 4 were made in a manner almost identical to that of example 6 of Table 2. The difference here is that various nonvolatile liquid or solid additives expected to perform as possible stabilizers were incorporated in the granulating liquid, i.e., ethyl alcohol, to make a solution or dispersion which was then used to granulate the drug/starch blend of each capsule formulation of examples 19–25, as done in the preparation of example 6 of Table 2.

Examples 26–31 listed in Table 5 are acetone granulations containing similar inactive power adjuvants and two different types of gabapentin containing 55 ppm of Cl⁻ anions after being treated with an alcoholic or an aqueous 0.005M HCl solution, i.e., purified-alc-HCl gabapentin or purified-aq-HCl gabapentin. Examples 26–31 of Table 5 were made in a manner almost identical to that of examples 10 or 11 of Table 2, depending on the type of the contained purified gabapentin, namely, purified-alc-HCl or purified-aq-HCl gabapentin. The difference here is that various nonvolatile liquid additives expected to perform as possible stabilizers were incorporated in the granulating liquid, i.e., acetone, to make a solution or dispersion which was then used to granulate the drug/starch blend of each capsule formulation of examples 26–31, as done in the preparation of examples 10 and 11 of Table 2.

Finally, examples 32–35 listed in Table 5 are aqueous granulations containing similar inactive powder adjuvants and two different types of gabapentin containing 55 ppm of Cl⁻ anions after being treated with an alcoholic or an aqueous 0.005M HCl solution, i.e., purified-alc-HCl gabapentin or purified-aq-HCl gabapentin. Examples 32–35 of Table 5 were made in a manner almost identical to that of examples 8 or 9 of Table 2, depending on the type of the contained purified gabapentin, namely, purified-alc-HCl or purified-aq-HCl gabapentin. The difference here is that nonvolatile liquid and solid additives expected to perform as possible stabilizers were incorporated in the aqueous granulating liquid to make a solution or dispersion which was then used to granulate the drug/starch blend of each capsule formulation of examples 32–35, as done in the preparation of examples 8 and 9 of Table 2.

Capsules of each formulation were placed in plastic High Density PolyEthylene (HDPE) plastic bottles without desiccant. The bottles were closed with metal caps and stored at accelerated and probe stability conditions, namely, at 40° C./75% RH and at 60° C./75% RH, respectively. Samples were withdrawn from both storage conditions at regular time intervals and analyzed for their drug and lactam contents using a fully validated, stability indicating HPLC method. The results are shown in Table 6 as the percent ratio of the weights of lactam and pure gabapentin found to be present in each stability sample at certain storage time intervals.

TABLE 6

| | % Lactam Detected | | | | | | | |
|---|---|---|---|---|---|---|---|---|
| | 60° C./75% Relative Humidity Days | | | | 40° C./75% Relative Humidity Days | | | |
| | 0 | 5 | 10 | 20 | 0 | 30 | 60 | 90 |
| Comp. Ex. A | 0.04 | 0.1 | 0.4 | 0.9 | 0.04 | 0.05 | 0.06 | 0.13 |
| Ex. 1 | 0.04 | 0.5 | 0.8 | 1.0 | 0.04 | 0.07 | 0.09 | 0.15 |
| Ex. 2 | 0.04 | 0.1 | 0.3 | 0.6 | 0.04 | 0.07 | 0.09 | 0.05 |
| Ex. 3 | 0.1 | 0.4 | 0.6 | 1.2 | 0.14 | 0.23 | 0.51 | 0.65 |
| Ex. 4 | 0.04 | 0.1 | 0.2 | 0.5 | 0.04 | 0.09 | 0.08 | 0.11 |
| Ex. 5 | 0.03 | 0.2 | 0.3 | 0.7 | 0.03 | 0.07 | 0.12 | 0.49 |
| Ex. 6 | 0.1 | 0.3 | 0.6 | 1.3 | 0.10 | 0.42 | 0.32 | 0.41 |
| Ex. 7 | 0.2 | 0.2 | 1.2 | 2.2 | 0.16 | 0.54 | 0.64 | 1.13 |
| Ex. 8 | 0.1 | 0.8 | 1.4 | 2.3 | 0.19 | 0.65 | 0.73 | 1.20 |
| Ex. 9 | 0.2 | 0.9 | 1.5 | 2.8 | 0.23 | 0.65 | 0.73 | 1.46 |
| Ex. 10 | 0.05 | 0.1 | 0.3 | 0.5 | 0.05 | 0.08 | 0.10 | 0.11 |
| Ex. 11 | 0.1 | 0.4 | 0.8 | 1.8 | 0.14 | 0.31 | 0.37 | 0.51 |
| Ex. 12 | 0.05 | 1.7 | 5.0 | 15.9 | 0.05 | 0.12 | 0.34 | 0.69 |
| Ex. 13 | 0.04 | 0.8 | 2.7 | 9.6 | 0.04 | 0.17 | 0.33 | 0.49 |
| Ex. 14 | 0.04 | 0.3 | 0.7 | 1.4 | 0.04 | 0.16 | 0.24 | 0.30 |
| Ex. 15 | 0.03 | 0.4 | 1.0 | 2.0 | 0.03 | 0.15 | 0.30 | 0.36 |
| Ex. 16 | 0.04 | 0.4 | 0.9 | 2.0 | 0.04 | 0.14 | 0.29 | 0.45 |
| Ex. 17 | 0.04 | 0.3 | 0.6 | 1.1 | 0.04 | 0.12 | 0.20 | 0.24 |
| Ex. 18 | 0.05 | SBM* | SBM* | SBM* | 0.05 | 0.24 | 0.70 | 3.91 |
| Ex. 19 | 0.1 | 2.3 | 6.2 | 15.9 | 0.11 | 0.42 | 1.01 | 1.84 |
| Ex. 20 | 0.1 | 1.3 | 3.4 | 11.6 | 0.14 | 0.41 | 0.66 | 1.25 |
| Ex. 21 | 0.1 | 0.4 | 0.9 | 2.1 | 0.09 | 0.26 | 0.39 | 0.55 |
| Ex. 22 | 0.1 | 0.7 | 1.4 | 2.9 | 0.10 | 0.33 | 0.58 | 0.85 |
| Ex. 23 | 0.1 | 0.7 | 1.2 | 2.9 | 0.10 | 0.32 | 0.49 | 0.82 |
| Ex. 24 | 0.1 | 0.6 | 1.0 | 1.9 | 0.11 | 0.31 | 0.50 | 0.69 |
| Ex. 25 | 0.1 | SBM* | SBM* | SBM* | 0.13 | 1.67 | 5.91 | 11.24 |
| Ex. 26 | 0.03 | 0.1 | 0.4 | 0.8 | 0.03 | 0.06 | 0.09 | 0.37 |
| Ex. 27 | 0.1 | 0.4 | 0.9 | 1.9 | 0.10 | 0.28 | 0.32 | 0.55 |
| Ex. 28 | 0.03 | 0.1 | 0.3 | 0.7 | 0.03 | 0.07 | 0.09 | 0.15 |
| Ex. 29 | 0.1 | 0.4 | 1.0 | 1.8 | 0.10 | 0.24 | 0.30 | 0.53 |
| Ex. 30 | 0.04 | 0.5 | 1.0 | 2.9 | 0.04 | 0.15 | 0.21 | 0.46 |
| Ex. 31 | 0.1 | 0.7 | 1.5 | 4.1 | 0.13 | 0.35 | 0.43 | 0.86 |
| Ex. 32 | 0.7 | SBM* | SBM* | SBM* | 0.65 | 7.85 | — | 26.50 |
| Ex. 33 | 0.9 | SBM* | SBM* | SBM* | 0.91 | 6.56 | 10.99 | 24.76 |
| Ex. 34 | 0.1 | 0.7 | 1.2 | 2.4 | 0.10 | 0.37 | 0.44 | 0.85 |
| Ex. 35 | 0.2 | 0.7 | 1.3 | 2.5 | 0.18 | 0.46 | 0.50 | 0.94 |

*Capsules turned into a solid brown mass (SBM).

The data of Table 6 show that stable solid dosage forms containing gabapentin and having more than 20 ppm Cl⁻ can be prepared in accordance with the present invention. In particular, referring to Table 6, example 2 was found to be more stable than examples 1 and 3 despite containing anhydrous gabapentin with more than 50 ppm of HCl. After storage at 40° C./75% RH for 3 months, the lactam impurity level of example 2 was less than 0.1%, which is less than the lactam level (0.15%) demonstrated by example 1 containing anhydrous gabapentin with less than 20 ppm of HCl. The exceptional stability of example 2 also illustrates that trace amounts of ethyl alcohol which remain within the final powder blend of the treated anhydrous gabapentin (i.e., purified-alc-HCl gabapentin) even after drying, are sufficient to provide a suitable stable dosage form.

The stability of the product developed using alcohol as the granulating liquid was significantly higher than that of products developed by water granulation or not treated at all. Specifically, the products containing gabapentin was more than 20 ppm Cl⁻ and treated with ethanol demonstrated a lactam impurity ranging from 0.6% to 0.9% after 10 days. On the other hand, products granulated with water only resulted in a lactam impurity of greater than 1.6%.

The stability-enhancing properties of ethyl alcohol are also seen by comparing the probe stability results of examples 1 and 2. After storage for 10 and 20 days at 60° C./75% RH, the alcohol-treated gabapentin containing more than 50 ppm HCl displayed lactam impurity levels approximately half of those displayed by the capsules containing gabapentin with less than 20 ppm HCl and not treated by alcohol. On the other hand, treatment with a polar solvent, such as water of example 3, did not provide the same stability enhancement on the gabapentin molecules containing more than 50 ppm HCl (i.e., purified-aq-HCl gabapentin). As shown in Table 6, after storage for 3 months at 40° C./75% RH, example 3 displayed a 0.65% lactam impurity.

Examples 4–11 illustrate that stable formulations of gabapentin are also obtained when the formulation are wet granulated. Example 10 was one of the most stable formulations of this group, despite containing anhydrous gabapentin with more than 50 ppm of HCl. After storage at 40° C./75% RH for 3 months, the lactam impurity level of example 10 was equal to 0.11%, which is identical to that displayed by example 4 containing anhydrous gabapentin with less than 20 ppm of HCl. The exceptional stability of example 10 establishes acetone as another preferred stabilizer in the present invention.

Furthermore, a comparison of the stability profiles of examples 10 and 11 illustrates a synergistic effect between ethyl alcohol and acetone in enhancing the stability of solid dosage forms containing gabapentin with more than 50 ppm of HCl. After storage at 40° C./75% RH for 3 months, the lactam impurity level of example 10 which was treated by both alcohol and acetone was only 0.11%, whereas example 11 which was treated with water and then acetone demonstrated a higher lactam level (0.51%). Nevertheless, the treatment with acetone subsequent to that of water conducted in example 11 still enhanced the stability of the final product as compared to that of example 9. The capsules of example 9 contain drug which, as in the case of example 11, was treated first by water (aqueous 0.005M HCl) to prepare the purified-aq-HCl gabapentin with 55 ppm of HCl. However, the granulation of example 9 was done with water, whereas the granulation of example 11 was done with acetone.

The data of Table 6 also show that treatment with alcohol as the granulating liquid enhances the stability of the final product, regardless of whether the anhydrous gabapentin with more than 50 ppm of HCl was initially treated with alcohol or water. In particular, after storage at 40° C./75% RH for 3 months, the lactam impurities of example 5 and 6, in which the drug has been initially treated by alcohol and water, respectively, followed by alcoholic granulation with corn starch, were at acceptable levels (0.49% and 0.41%, respectively). On the other hand, the aqueous granulations of example 7, containing gabapentin with less than 20 ppm of HCl and not treated initially by water or alcohol, and examples 8 and 9, containing gabapentin with more than 50 ppm of HCl which has been treated initially by alcohol or water, respectively, demonstrated higher lactam levels after storage at 40° C./75% RH for 3 months (1.13%, 1.20% and 1.46%, respectively).

Granulation treatment with ethyl alcohol also induces stability enhancement in capsule formulations containing anhydrous gabapentin with less than 20 ppm of HCl. After storage at 40° C./75% RH for 3 months, the lactam impurity level of example 1, which is a dry blend of the originally received drug with two powder adjuvants, was equal to 0.15%. In comparison, example 4, which is an alcoholic granulation of the same drug and powder excipients, demonstrated a lower lactam level (0.11%). In addition, after storage at 60° C./75% RH for 10 and 20 days, the lactam levels of example 1 were equal to 0.8% and 1%, respectively, whereas the lactam levels of example 4 were 0.2% and 0.5%, respectively.

The stability profiles of examples 12–18 may be compared to those of example 5 to assess the degree of stability enhancement provided by various additives included in the corresponding capsule formulation. As shown in Table 6, after storage at 40° C./75% RH for 3 months, examples 12–17 demonstrated relatively low lactam levels, which illustrate that the stability enhancement, already known to be promoted by the alcoholic treatments of the drug and the granulation, is maintained or even improved by the addition of Butylated Hydroxyanisole (Ex. 12), a combination of Povidone and Butylated Hydroxyanisole (Ex. 13), Polysorbate 80 (Ex. 14), Polyethylene Glycol 400 (Ex. 15), a combination of Polyethylene Glycol 400 and Silica (Ex. 16) and Propylene Glycol (Ex. 17).

The stability profiles of examples 19–25 may be compared to those of example 6 to further assess the degree of stability enhancement provided by various stabilizers included in the corresponding formulation. After storage at 40° C./75% RH for 3 months, examples 21 and 24 demonstrated relatively low lactam levels, illustrating that the stability enhancement, already known to be promoted by the aqueous treatment of the drug followed by subsequent alcoholic granulation, is maintained by the addition of Polysorbate 80 (Ex. 21) and Propylene Glycol (Ex. 24).

In addition, the stability profiles of examples 26, 28 and 30 can be compared to those of example 10, all of which contain purified-alc-HCl gabapentin prepared using acetone alone as the granulating liquid, to assess the degree of stability enhancement provided by various stabilizers. After storage at 40° C./75% RH for 3 months, example 28 containing Propylene Glycol as the additive, demonstrated an extremely low lactam level (0.15%), similar to that displayed by example 10 (0.11%). Furthermore, after storage at 40° C./75% RH for 3 months, examples 26 and 30, containing olive oil and Polyethylene Glycol 400, respectively, as the additives, also demonstrated acceptably low lactam levels (0.37% and 0.46%, respectively). These findings illustrate that the stability enhancement, already known to be promoted by the alcoholic treatment of the drug and its subsequent granulation with acetone (example 10), is maintained by the addition of Propylene Glycol (example 28).

Similar conclusions can be drawn by comparing the stability profiles of examples 27, 29 and 31, containing olive oil, Propylene Glycol and Polyethylene Glycol 400 as nonvolatile liquid stabilizers, with that of example 11, containing purified-aq-HCl gabapentin prepared using acetone alone as the granulating liquid. After storage at 40° C./75% RH for 3 months, the capsule formulations of examples 27, 29, and 31 demonstrated lactam levels (0.55%, 0.53% and 0.86%, respectively) which are similar to those of example 11 (0.51%). Consequently, the relative stability enhancement, already known to be promoted by the aqueous treatment of the drug and its subsequent granulation with acetone (example 11), is maintained by the addition of olive oil (example 27) and Propylene Glycol (example 29).

The stability profile of example 34 may be compared to that of example 8, each of which contain purified-alc-HCl gabapentin prepared using water alone as the granulating liquid, to assess the degree of stability enhancement provided by Propylene Glycol. As shown in Table 6, after storage at 40° C./75% RH for 3 months, example 34, containing Propylene Glycol as the additive nonvolatile liquid, demonstrated a lactam level equal to 0.85%, which is significantly lower than that displayed by example 8 (1.20%).

Similarly, the stability profile of example 35 may be compared to that of example 9, each of which contain purified-aq-HCl gabapentin prepared using water alone as the granulating liquid, in order to assess the degree of stability enhancement provided by Propylene Glycol. After storage at 40° C./75% RH for 3 months, example 35, containing Propylene Glycol as the additive nonvolatile liquid, demonstrated a lactam level equal to 0.94%, which is significantly lower than that displayed by example 9 (1.46%).

In conclusion, the capsule formulations of examples 1–35 prepared and tested have clearly demonstrated that the stability of an amino acid, such as gabapentin, known to degrade via cyclization can be markedly improved if the amino acid alone or in combination with inactive powder adjuvants of the solid dosage form is treated with certain pharmaceutically acceptable liquid and/or solid stabilizers. These stabilizers can be various semipolar or nonpolar, volatile or nonvolatile liquids and solids which are expected to drastically reduce or almost completely inhibit the ionic activity and electronegativity of various anions of mineral acids possibly attached to the crystalline or amorphous structure of the amino acid as remains of its original synthesis and purification. Due to their extremely high ionic and ionizable characters, such anions (e.g., $Cl^-$) of mineral acids (e.g., HCl) display the tendency to attract water away from the molecules of the amino acid resulting in its solid state dehydration and cyclization to its corresponding lactam impurity. The data further show that small quantities, or even trace amounts, of said stabilizers can significantly enhance the stability properties of amino acids formulated in a solid dosage form regardless of the concentration of destabilizing anions in the amino acid.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true scope and spirit of the invention.

What is claimed is:

1. A method of preparing stable pharmaceutical formulations in dry dosage form comprising the steps of:
    dissolving a mineral acid in a stabilizer,
    wetting gabapentin with the mineral acid solution, and
    removing a substantial portion of the stabilizer to form gabepentin crystals
comprising gabapentin molecules and a mineral acid present in an amount to provide at least 20 ppm of an anion of the mineral acid, based on the weight of gabapentin, said mineral acid dispersed throughout each gabapentin crystal, wherein said formulation contains less than 1% by weight of the lactam degradation product of gabapentin after being stored for 3 months at 40 degrees Centigrade and 75% relative humidity.

2. The method of claim 1 wherein the stabilizer is ethanol, acetone, isopropyl alcohol, or methanol.

3. The method of claim 1 wherein the stabilizer is ethanol.

4. The method of claim 1 wherein the anion of a mineral acid is chloride ions.

5. The method of claim 1 wherein the mineral acid is present in an amount to provide from 20 ppm to about 55 ppm of the anion of the mineral acid, based on the weight of gabapentin.

6. The method of claim 1 wherein the mineral acid is present in an amount to provide from 20 ppm to about 40 ppm of the anion of the mineral acid, based on the weight of gabapentin.

7. The method of claim 1 wherein the dry dosage form further comprises at least one pharmaceutically acceptable adjuvant.

8. The method of claim 1 wherein the stabilizer is a volatile organic liquid with a dielectric constant below 60.

9. The method of claim 1 further comprising the step of:
    dry-mixing the gabapentin crystals with a pharmaceutically acceptable adjuvant.

10. The method of claim 1 wherein the mineral acid in each crystal of gabapentin is uniformly dispersed.

11. A method of preparing stable pharmaceutical formulations in dry dosage form comprising the steps of:
    dissolving a mineral acid in a stabilizer,
    wetting a cyclic amino acid which is susceptible to formation of a lactam with the mineral acid solution, and
    removing a substantial part of the stabilizer to form crystals of the cyclic amino acid, said crystals comprising the cyclic amino acid and a mineral acid present in an amount to provide at least 20 ppm of an anion of the mineral acid, based on the weight of the cyclic amino acid, said mineral acid dispersed throughout each crystal of the cyclic amino acid, wherein said formulation contains less than 1% by weight of the lactam after being stored for 3 months at 40 degrees Centigrade and 75% relative humidity.

12. The method of claim 11 wherein the dry dosage form further comprises at least one pharmaceutically acceptable adjuvant.

13. The method of claim 11 wherein the stabilizer is ethanol, acetone, isopropyl alcohol, or methanol.

14. The method of claim 11 wherein the stabilizer is ethanol.

15. The method of claim 11 wherein the anion of a mineral acid is chloride ions.

16. The method of claim 11 wherein the mineral acid is present in an amount to provide from 20 ppm to about 55 ppm of the anion of the mineral acid, based on the weight of gabapentin.

17. The method of claim 11 wherein the mineral acid is present in an amount to provide from 20 ppm to about 40 ppm of the anion of the mineral acid, based on the weight of gabapentin.

18. The method of claim 11 wherein the stabilizer is a volatile organic liquid with a dielectric constant below 60.

19. The method of claim 11 further comprising the step of:
    dry-mixing the cyclic amino acid crystals with a pharmaceutically acceptable adjuvant.

20. The method of claim 11 wherein the mineral acid in each crystal of gabapentin is uniformly dispersed.

* * * * *

UNITED STATES PATENT AND TRADEMARK OFFICE
CERTIFICATE OF CORRECTION

| | | |
|---|---|---|
| PATENT NO. | : 7,056,951 B2 | Page 1 of 1 |
| APPLICATION NO. | : 09/928467 | |
| DATED | : June 6, 2006 | |
| INVENTOR(S) | : Spiridon Spireas | |

It is certified that error appears in the above-identified patent and that said Letters Patent is hereby corrected as shown below:

Title Page,
Item [56], References Cited, U.S. PATENT DOCUMENTS,
Delete "6,531,509 B1" and insert -- 6,531,509 B2 --.

Column 5
Line 57, delete "wight;" and insert -- weight; --.

Signed and Sealed this

Twenty-third Day of January, 2007

JON W. DUDAS
*Director of the United States Patent and Trademark Office*